(12) United States Patent
Sarrazin et al.

(10) Patent No.: US 7,113,265 B1
(45) Date of Patent: Sep. 26, 2006

(54) POWDER HANDLING DEVICE FOR ANALYTICAL INSTRUMENTS

(75) Inventors: Philippe C. Sarrazin, Palo Alto, CA (US); David F. Blake, Los Altos, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/808,704

(22) Filed: Mar. 17, 2004

Related U.S. Application Data

(60) Provisional application No. 60/472,359, filed on May 20, 2003.

(51) Int. Cl.
*G01N 21/64* (2006.01)
*G01N 21/65* (2006.01)
*G01N 21/85* (2006.01)

(52) U.S. Cl. .................... 356/73; 356/301; 356/317; 356/244; 356/440

(58) Field of Classification Search ............ 356/73, 356/301, 317, 318, 440, 244
See application file for complete search history.

(56) References Cited

U.S. PATENT DOCUMENTS

| | | | | |
|---|---|---|---|---|
| 3,914,604 A | * | 10/1975 | Hornby et al. | 378/51 |
| 4,055,076 A | * | 10/1977 | Tropea | 356/427 |
| 4,265,544 A | * | 5/1981 | Banno et al. | 356/427 |
| 4,372,683 A | * | 2/1983 | Sternberg | 356/427 |
| 4,373,931 A | * | 2/1983 | Takekawa | 356/246 |
| 5,491,738 A | | 2/1996 | Blake et al. | |
| 6,064,717 A | | 5/2000 | Ortega et al. | |
| 6,508,104 B1 | | 1/2003 | Deluca et al. | |
| 6,598,466 B1 | | 7/2003 | Deluca et al. | |
| 2003/0110871 A1 | | 6/2003 | Matachowski et al. | |

* cited by examiner

*Primary Examiner*—F. L. Evans
(74) *Attorney, Agent, or Firm*—John F. Schipper; Robert M. Padilla; Diana M. Cox

(57) ABSTRACT

Method and system for causing a powder sample in a sample holder to undergo at least one of three motions (vibration, rotation and translation) at a selected motion frequency in order to present several views of an individual grain of the sample. One or more measurements of diffraction, fluorescence, spectroscopic interaction, transmission, absorption and/or reflection can be made on the sample, using light in a selected wavelength region.

25 Claims, 9 Drawing Sheets

POWDER HANDLING DEVICE FOR ANALYTICAL INSTRUMENTS

ORIGIN OF THE INVENTION

This application claims a benefit of priority from U.S. Provisional Application No. 60/472,359, filed May 20, 2003, the entire disclosure of which is herein incorporated by reference.

The invention described herein was made by employees of the United States government in the performance of work under contracts with the United States National Aeronautics & Space Administration (NASA) and is subject to the provision of Section 305 of the United States National Aeronautics and Space Act of 1958, Public Law 85-568 (72 Stat. 435; 42 U.S.C. 2457).

The present invention may be manufactured and used by or for the United States Government for governmental purposes without payment of any royalties thereon or therefore.

TECHNICAL FIELD OF THE INVENTION

This invention relates to a device for and method of handling powder samples in conjunction with an analytical instrument, such as an X-ray diffractometer.

This invention describes a powder handling device for analytical instruments that places the powder in motion during analysis using vibrations at sonic or ultrasonic frequencies.

This invention is related to automation of sample handling and movement such that coarse-grained powder or other solid materials can be analyzed by a robotic or totally computer automated analytical system. As used in this specification, the term "sample" refers to any organic or inorganic molecule, which may be crystalline, that is prepared or directly obtained from a collected portion of material to be analyzed. "Sample preparation" is the physical transformation of the collected material to make it usable for X-ray diffraction (XRD), X-ray fluorescence (XRF) or other analytical means. Such physical transformation process can be crushing, grinding, milling, sieving, or the like. This process results in a powder material that can be analyzed by XRD, or other powder analytical techniques. "Sample handling" is the manipulation of the sample to transport it and present it in the instrument in an appropriate manner.

All powder XRD instruments require an extremely fine-grained, powder sample (<<50 micrometers ($\mu m$) grain size). This sample constraint has traditionally presented a major impediment to deployment of XRD on spacecraft missions, or other missions involving remote or difficult analytical environments.

In the approach described herein, the powder is handled as a fluid, using mechanical vibrations in conjunction with a driving force (gravity or gas flow) and requires few or no moving parts. The major improvements over conventional sample handling techniques for XRD are the simplicity of the system, its suitability for in situ applications, and the potential to characterize larger grain-size material, resulting in a significant relaxation of the constraints on sample preparation (grinding).

This powder handling system as described extends the range of useful grain sizes for XRD/XRF from a few $\mu m$ to several hundred $\mu m$. Development of the powder handling system can be extended to enable robotic, or totally computer automated systems, such as the CheMin system, which is a totally computer automated/robotic XRD/XRF instrument designed and developed by NASA to directly analyze samples, from rock crushers in remote applications like Antarctica, the NASA Mars Science Laboratory, or in other extreme, toxic or hazardous environments. The CheMin system is described in U.S. Pat. No. 5,491,738, which is incorporated by reference herein.

The key role that definitive mineralogy plays in Mars missions, or Earth geological missions, is a consequence of the fact that minerals are thermodynamic phases, having known and specific ranges of temperature, pressure and composition within which they are stable. Going beyond simple compositional analysis, definitive mineralogical analysis can provide information about pressure/temperature conditions of formation, past climate, water activity, the fugacity (activity) of biologically significant gases and the like.

Minerals are identified as unique structural and compositional phases that occur naturally. There are about 15,000 minerals on Earth that have been described, and each of these phases is uniquely identified by its XRD pattern. There are likely many minerals yet undiscovered on Earth, and likewise on Mars. If an unknown phase is identified on Mars or in Earth geological studies, it can be fully characterized by structural (XRD) and elemental (XRF) analysis without recourse to other data, because XRD relies on the first principles of atomic arrangement for its determinations, and XRF relies on first principles of electron binding energies of inner and outer shell electrons for its determinations.

Other applications of XRD/XRF include the following: (1) laboratory XRD and/or XRF analysis for samples that do not qualify as "fine;" (2) process control in manufacture of pharmaceutical compounds; and (3) industrial characterization of cement and mining materials.

Because a near-infinite number of orientations of crystallites to the beam is needed to produce an interpretable pattern, powder samples are required for XRD. Sample preparation has thus been a principal hindrance to deployment of XRD on robotic missions for remote locations or hostile environments.

The innovative described sample movement system relaxes constraints on longstanding requirement for fine-grained powder for XRD analysis. This is a particularly timely and urgently needed technology because often sample preparation devices do not produce fine-grained samples that are suitable for XRD analysis. Without the powder movement system described herein, totally automated, remotely operated XRD/XRF systems are much more complex, and difficult to implement.

Other benefits of this invention include:
  (i) improvement of the quality of solid/powder analysis by exposing more material to the detector;
  (ii) improvement of the quality of the analysis by randomly rotating the grains of powder to expose all orientations to the detector;
  (iii) enablement of automatic specimen preparation or manual specimen preparation of powder samples in difficult conditions;
  (iv) enablement of automatic loading of the powder sample into the instrument; and
  (v) isolation of the sample from the environment, so that reactive or dangerous materials can be safely analyzed.

This invention applies to analytical instruments that analyze powder samples.

BACKGROUND OF THE INVENTION

Many analytical instruments require a powder sample: to control the shape and/or volume of the specimen; to increase the surface area of the specimen; to increase the statistical representation of a specimen when samples are not homogeneous with regard to the characterized property; and/or to increase the statistical representation of the specimen spatial orientation when the properties being characterised are not equivalent in different viewing directions.

In one embodiment of the invention, the instrument is an X-ray diffraction apparatus, as the invention is particularly suited to X-ray instruments that utilize small X-ray beams, such as non-focused or miniature X-ray diffraction instruments.

The powder sample handling technique would also find application with instruments using techniques other than X-ray diffraction. Non restrictive examples of such application are listed herein:

X-ray fluorescence: the analysis consists in measuring the X-ray emission spectrum of the sample when the sample is irradiated by X-rays. If selected energies or white (continuous) X-rays are used to illuminate the sample, inner electrons shells of the constitutive atoms can be excited and emit X-ray radiation at characteristic wavelengths. Measuring the emission spectrum allows identifying the nature and abundance of the constitutive atoms. The powder handling system would be used to insert the sample in the analysis region and randomize the sample during analysis. This would enable complete automation of the analysis with no need to prepare pellets of the powder sample usually done.

Infrared absorption spectroscopy: the analysis consists in measuring the absorption (attenuation) of infrared light passing through a sample depending on the wavelength of the radiation. Chemical bonds in the sample can vibrate at particular frequencies (i.e. with particular energies) and consequently can absorb particular electromagnetic energies. As a consequence, measuring the energies (or wavelength) that are absorbed by a compound allows identification of chemical bounds and in turn identification of the compound. Powder samples are typically used and are ground to fine grain (<2 µm) to limit scattering of incident light. The sample is analyzed in a solid or liquid matrix for index matching. The powder handling technique could be applied to either dry sample, or preferably powders sample in suspension in an appropriate liquid. The sample handling technique would ease manual loading of the sample and enable automatic/robotic operation of the infrared spectrometer. It would also allow randomization of samples and analysis of large quantities of material, or analysis of a stream of material.

Raman spectroscopy of powder sample: Raman spectroscopy consists in the measurement of the wavelength of backscattered radiation of a sample illuminated by a monochromatic radiation usually produced by a laser. Identification of particular wavelength shifts (Raman shift) allows identification of the compound, based on its particular molecular vibrations and/or its crystalline vibrations. The powder handling system can be used in conjunction with a Raman spectrometer to allow automatic loading of powder in the spectrometer, randomize the sample during analysis, and analyze a larger quantity of powder that would be analyzed by conventional techniques.

Microscopic imaging of powder sample: The powder handling system would be used to load the sample in the imaging region of a microscope. Imaging can be done in reflection or transmission mode, on dry powders or with the sample placed in suspension in a liquid.

Imaging particle size analyzer: The powder sample is vibrated for insertion in the imaging region consisting of two windows separated with a distance of the order of the diameter of the largest grains of powder. The vibration amplitude is adjusted so that the grains of powder have a level of excitation spreading them apart. When the vibration is stopped, the grain motion stops. An image of the sample is then collected, in reflection or, preferably, in transmission mode, using a camera equipped with high magnification optics or mounted on a microscope. The image collected is transferred to a computer equipped with an image analysis software that characterizes the size and shape of the grains observed on the image. The sample is then vibrated to randomize the sample. Vibration is stopped and a new image is acquired. After analysis of a sufficient number of images, size and/or shape distributions of the sample are obtained by summing the data of individual image analysis.

However, one of the most demanding analytical techniques, with regard to preparation of powder sample for analysis, is XRD.

XRD, the most common technique for studying crystal structures, is applied in many fields such as geology for identifying minerals, material sciences for studying materials structures and quantifying structural strain, biochemistry for studying macromolecular structures and identifying pharmaceutical compounds, archaeology for investigating localities and processes of fabrication of artifacts, as well as many other applications.

XRD relies on the measurement of the angles at which crystalline matter constructively reflects X-rays from a set of atomic layers defined by the crystal structure. Each crystal structure has a set of possible reflections that occur when the crystal is appropriately oriented in an X-ray beam. Measuring all the possible reflections of a sample in an angular range allows determination of the sample crystalline structure, or the actual sample identification based on its crystalline structure.

Performing an XRD analysis requires exploring all the possible orientations of a crystal and measuring the conditions at which reflections occur within a practical angular range. One approach is to use a single crystal that is rotated in an X-ray beam to expose all possible orientations, but this is mechanically complex, and in terms of size for remote locations, is very impractical.

The most common approach of XRD, called powder diffraction, uses powder material, or solid polycrystalline material, to create a specimen that offers all possible crystalline orientations without requiring complex sample movement. It is assumed that the specimen is composed of a large number of crystals, identical in structure and oriented in all directions so that all of the possible orientations leading to the reflection of X-rays are statistically well represented. Quality powder diffraction data can only be obtained with fine grained powders (less than about 10 µm in diameter), because relatively fine grains such as these lead to a better statistical representation of the crystal orientation within the finite volume exposed to the incident radiation. This is the case for all powder diffraction instruments, but is particularly important for instruments for which the volume of material under X-ray illumination is very small, such as miniature instruments and instruments that are not based on focused/parafocused geometries. These instruments are very sensitive to the grain size of the powder, with the quality of the data being dramatically altered as the grain size increases.

Grinding the material down to an ideal grain size is sometimes impossible, and conditioning the sample for analysis is often time consuming and labor intensive. Further, for operation in remote or extreme environments, neither of these approaches are acceptable.

BACKGROUND ART

In U.S. Application, 20030110871 A1, filed Dec. 13, 2001, published Jun. 19, 2003, a system for analyzing particles is described, including: a source of solid particles; a sampler apparatus attached to and integral with the source of solid particles which apparatus is adapted to enable removal of small amounts of sample material from the source; a sonication cell connected to the sampling apparatus which sonication cell receives, optionally conditions, and sonicates the small amounts of sample material; a sample analysis apparatus connected to the sonication cell which sample analysis apparatus is adapted to receive, optionally further condition, and analyze the resulting sonicated sample; and, a liquid pump and liquid carrying lines adapted to: withdraw aliquots from the source; convey a withdrawn aliquot to the sonication cell and sample analysis apparatus; and, flush the system free of residual aliquot contamination.

In U.S. Pat. No. 6,508,104, filed Oct. 5, 2000 and issued Jan. 21, 2003, and U.S. Pat. No. 6,598,466, filed Oct. 5, 2000 and issued Jul. 29, 2003 to DeLuca et al, methods are described for sonicating a liquid suspension of first particles; and analyzing the liquid phase for second particles; and, an apparatus including a sonicator and an analyzer, purpose of which is to analyze the adhesion force relationships between the main or host first particles and guest or surface additive second particles.

In U.S. Pat. No. 6,064,717, filed Nov. 21, 1997, issued May 16, 2000 to Ortega, an unrestricted motion device having a sample holder, a detctor holder capable of independent multidimensional movement, a radiation source and a radiation source holder, also capable of independent, multidimensional movement in which the preferred embodiment of the holders are robots is described. This invention teaches the replacement of prior art goniometers with individual independent robots, such that the sample holder is not physically attached or coupled to the robot moving the detector or the robot moving the radiation source. Therefore, the restrictions on sample size, weight and shape are removed. Also, restrictions on coverage of reciprocal space are greatly reduced since the detector, radiation source and/or sample holder can be moved out of plane to any location in the robot's accessible envelope of reach. Also, the need for numerous sample holders capable of different axial motions is eliminated and automatic sample changing and tube changing from point to line mode is enabled.

What is needed is an approach that allows use of relatively large grain size samples (up to a few hundred μm in diameter) for XRD and XRF analysis and allows use of a wide range of wavelengths to interrogate a sample. Preferably, the approach should allow use of two or more wavelengths simultaneously and should allow performance of XRD analysis and XRF analysis simultaneously on a sample.

SUMMARY OF THE INVENTION

These needs are met by the invention, which provides a sample holder having at least one sample window that is substantially transparent to electromagnetic radiation in a selected wavelength region. At least one of the sample holder, the sample window and the sample may be caused to vibrate and/or translate and/or rotate at each of one or more selected frequencies in the sonic and/or ultrasonic range, and the sample is interrogated through the window by radiation in the selected wavelength region (infrared, visible and/or X-ray, referred to collectively as "light" herein), and one or more measurements of diffracted light, reflected light, transmitted light, absorbed light and/or infrared spectroscopic information is performed as the sample holder, sample window and/or sample is vibrated at the selected frequency. The time interval for interrogation may have a length of from a few sec to a few minutes, or longer if desired.

A system constructed and operated according to the invention includes a specimen holder that is constructed to contain or support grains of (dry) powder material (a sample) to be analyzed by the analytical instrument, and is further constructed to place such grains in motion. In one embodiment, the motion is produced by subjecting the grains to sonic or ultrasonic frequency vibrations, produced by vibration generating means such as one or more actuators.

In one embodiment, the analytical instrument is an XRD instrument and the analysis is performed through a window. The material of the window has a low-absorption coefficient for the radiation of interest to limit the signal reduction by absorption in the window.

In another embodiment, the analytical instrument is an instrument for performing XRF or infrared spectroscopiy, and the analysis is performed in a transmission mode.

The invention also provides means for adjusting the density or compactness of the powder: High intensity vibration provides particle dispersion, and low intensity vibration provides particle compaction. This is especially useful for transmission XRD instruments, which benefit from having the sample optimized with respect to interaction with the X-rays of interest.

These and other embodiments of the invention are illustrated in the following FIGS. 1–8, which are provided as non-limiting embodiments of the invention. The Figures illustrate the methods for achieving X-ray diffraction analysis of powder mineral samples by subjecting such sample to sonic or ultrasonic vibrations while the samples are also subjected to irradiation with X-rays and measuring the diffraction of such X-rays; the capability for automatic specimen preparation or manual specimen preparation in difficult conditions; and the way in which the internal compartment of the sample holder can be isolated from the environment (sealed sample holders), so that reactive or dangerous materials can be safely analyzed.

This invention also applies to other types of analytical instruments such as X-ray fluorescence spectrometers, infrared spectrometers, optical microscopes and, in general, all types of analytical instruments that characterize powder samples. The actual benefits of the invention to a specific instrument depend on the nature of the instrument.

In one embodiment, the instrument can perform the analysis through a window or film and the powder sample is isolated from the environment, allowing safe handling and analysis of dangerous or reactive material.

This invention provides an alternative approach of specimen preparation that is not labor intensive and permits acquisition of quality data, even when the powder is not of the optimum grain size.

DESCRIPTION OF BEST MODES OF THE INVENTION

Figure 1:
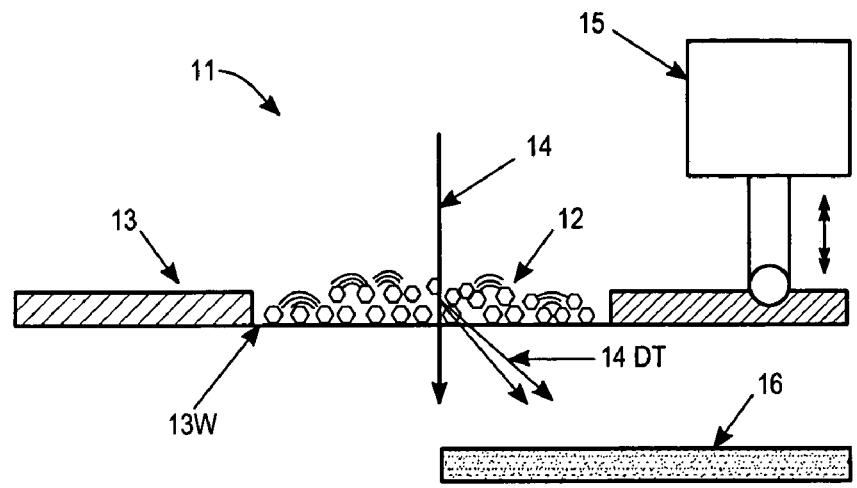
FIGS. 1, 2, 4, 5, 6 and 7 illustrate some embodiments of the invention.

The basic principle of the invention is to handle powder as a fluid by using mechanical vibrations in conjunction with a driving force such as gravity or a slow gas flow. In the simplest versions for only powder handling system (PHS) functions, no moving parts are required, while more complex versions would require a limited number of moving parts. The power requirement can be very low and the system can be compact enough to be fitted inside a miniature XRD instrument. While the PHS is developed primarily for XRD application, other techniques might benefit from an automated powder handling system, and the technology could be used to deliver samples to other types of analytical instruments.

The approach is not restricted to use of a particular analysis system, such as the NASA CheMin instrument. The approach is applicable to virtually all types of powder XRD systems, whether based on transmission or reflection geometry. This approach can be used for XRD and/or XRF measurements in remote, hazardous and/or extreme environments.

The invention provides a device and method for handling a powder sample during the course of an analysis so that internal motion within the sample and/or global motion of the sample through the specimen holder are implemented, without generating significant changes in the geometry and the position of the sample with respect to the beam and detector.

The method described offers an alternative approach to expose more material to the analytical volume and to provide a better representation of spatial orientations of the grains, by inducing vibrations in the sample through an actuator such as a piezoelectric device. The vibrational energy is received by the powder sample, which then behaves as a fluid.

Where no driving force is applied to the sample, this excitation will merely result in a Brownian-like motion of the grains. This alone can be beneficial to the XRD analysis as grains would rotate slightly, and present more crystalline orientations to the incident beam.

However, if a driving force is present, such as gravity, or a controlled gas flow, the fluidization can be used to generate macroscopic motion of the sample. Moving the grains during an analysis has two consequences: (i) the total amount of material analyzed is increased; and (ii) random rotations and/or translations expose each grain to the beam under different orientations over the time interval of the analysis.

For XRD, this approach improves the fidelity of a sample and permits acquisition of good data even when coarse grained materials are being analyzed.

Random motion of the individual grains is obtained by placing the powder in, or making it flow through, a sample holder that includes at least one transparent surface, such as a window, or film, and causing the sample to vibrate at sonic or ultrasonic frequencies by means of an actuator (piezoelectric, electromagnetic, mechanical or the like).

Several types of movement can be generated with this system:

1. Random short range motion of the grains (FIGS. 1 and 2).
2. Granular convection that occurs naturally in gravity when granular material is vibrated (FIG. 3).
3. Directional flow driven by gravity (FIGS. 4 and 5).
4. Directional flow driven by flow of gas inside the sample holder (FIG. 6).
5. Directional flow driven by controlled wave propagation inside the sample holder (FIG. 7).

FIG. 1 illustrates a sample holder 11 that allows random rotation and translation of the grains of a powder sample 12 shown in conjunction with a transmission geometry XRD instrument. The actuator vibrates a plate 13 that includes a window 13W that is transparent to electromagnetic radiation 14 in a selected wavelength region (e.g., a portion of the infrared spectrum, the visible spectrum or the X-ray spectrum). The radiation 14, incident on the sample 12, provides diffracted or transmitted radiation 14DT that is received by a radiation detector 16. Vibration provided by an actuator 15 is transmitted to the sample by the plate 13 and/or window 13W, resulting in random motion of the grains 12. Alternatively, the sample grains may be vibrated by the actuator 15. The actuator 15 is configured to provide an excitation mode perpendicular to the plane of the window 13W, but a parallel excitation mode and other excitation configurations can also be used.

Figure 2:
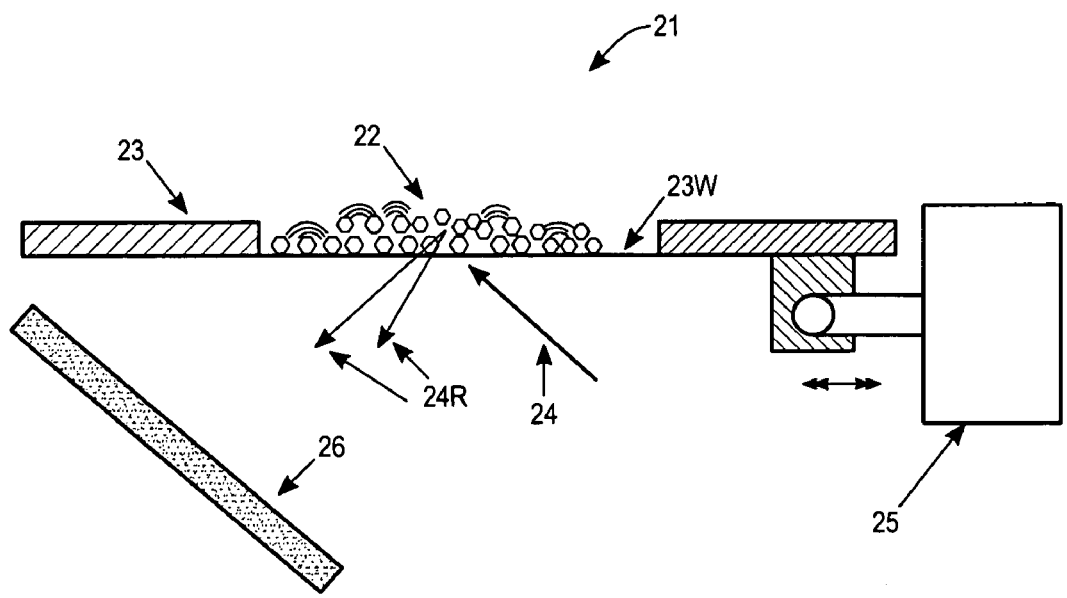

FIG. 2 illustrates a sample holder 21 that allows random rotation and translation of the grains of a powder sample 22. The sample 22 rests on a transparent window 23W that is part of a plate 23 that is rotated and/or translated by an actuator 25 in a parallel (or perpendicular) excitation mode. Electromagnetic radiation 24, incident on the sample, 22, provides reflected light that is received by a detector 26.

Figure 3B:
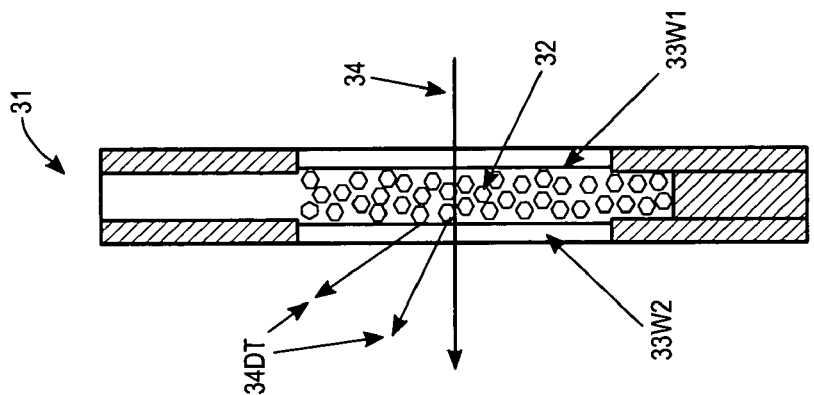
FIGS. 3A, 3B and 8 illustrate sample holders constructed according to the invention.
Figure 3A:
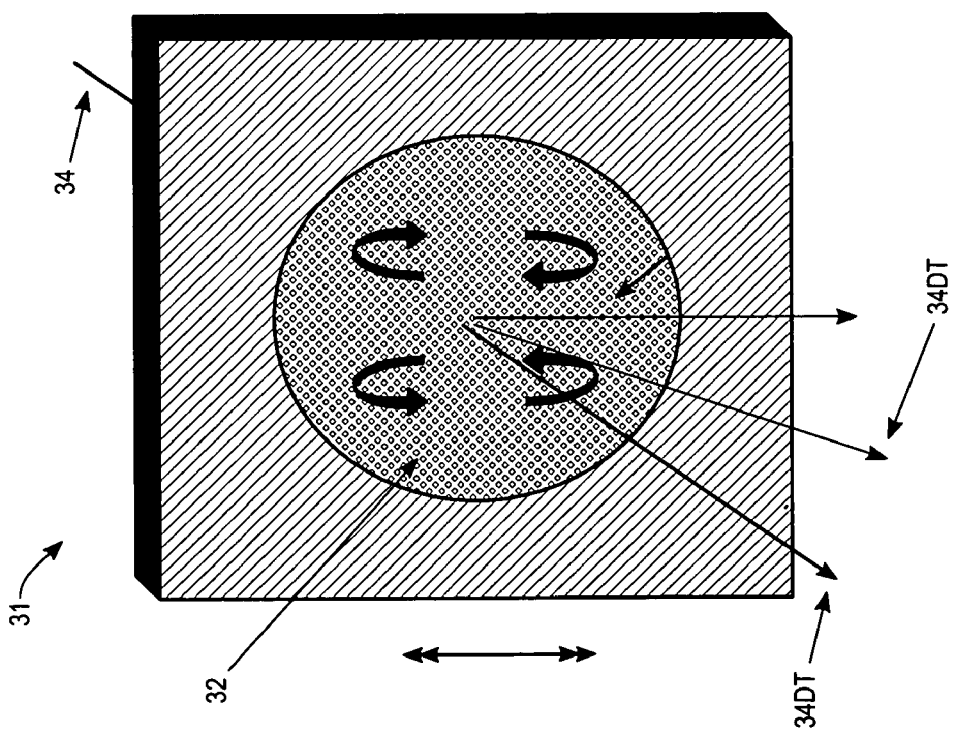

FIGS. 3A and 3B are a front view and a sectional side view, respectively, of a sample holder 31, showing granular convection of the grains of a powder sample 32. The sample holder 31 includes first and second transparent windows, 33W1 and 33W2, that are spaced apart by 10–1000 µm and face each other, with the sample 32 being positioned between the first and second windows. An actuator (not shown) provides vibration of the sample 32. Electromagnetic radiation 34 in a selected wavelength region is incident on and passes through the first window 33W1, the sample 32 and the second window 33W2 to provide diffracted or transmitted light 34DT that is received by a detector (not shown).

Figure 4:
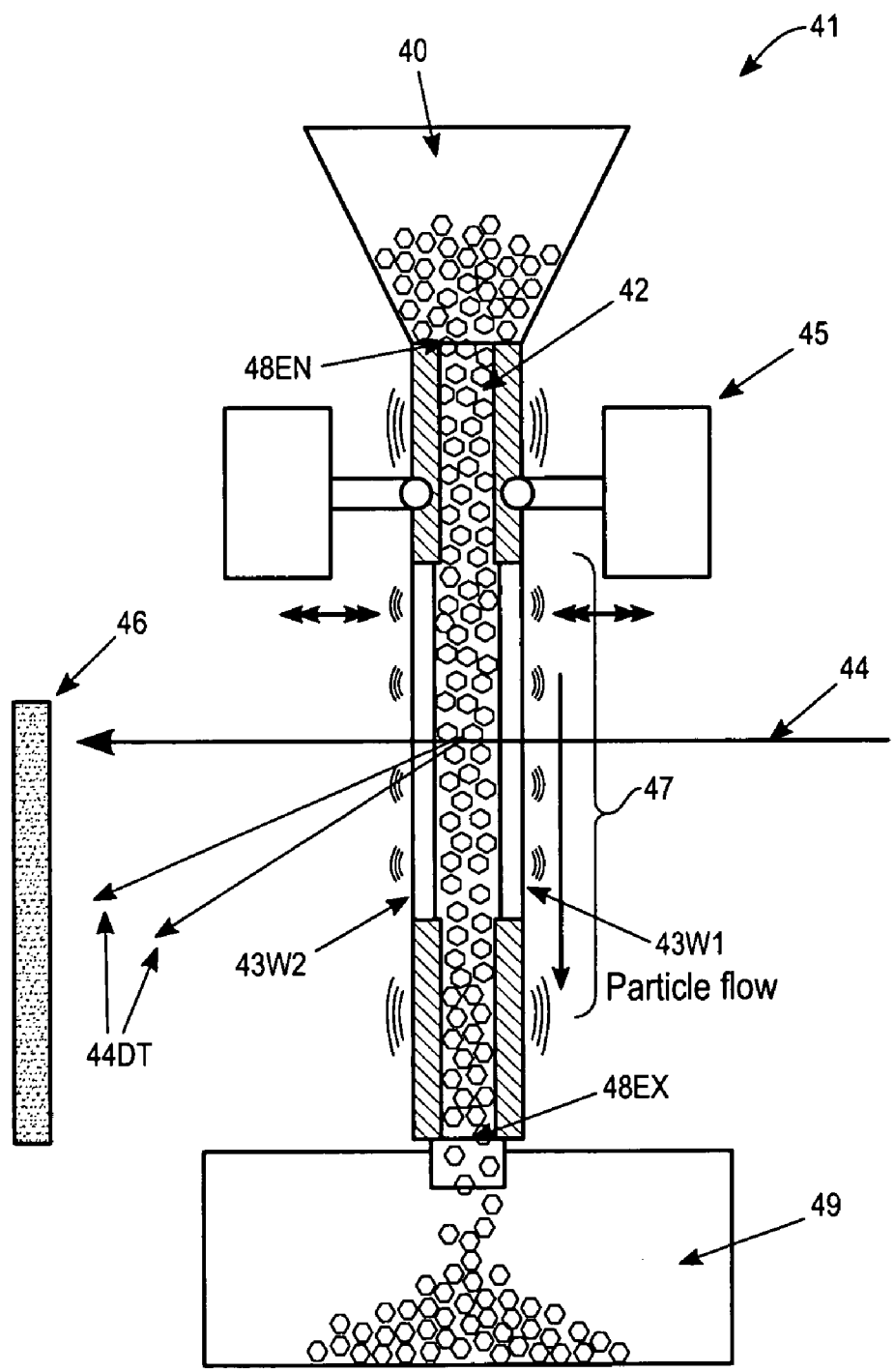

FIG. 4 is a sectional side view of a sample holder 41 that provides a flow of a powder sample 42 from a reservoir 40, using a selected combination of gravity-induced flow and vibration-induced flow, provided by an actuator 45 operating in a perpendicular or parallel mode of excitation. The sample 42 flows in a narrow channel 47, defined by two transparent windows, 43W1 and 43W2, that are spaced apart by 10–1000 µm and face each other, which has an entrance aperture 48EN and an exit aperture 48EX through which the sample 42 passes. Vibration and gravity result in an overall flow of material, in addition to random motion of the grain and convective internal flows. Electromagnetic radiation 44 in a selected wavelength region is incident on the first and second windows, 43W1 and 43W2, and the portion of the sample 42 contained between the first and second windows. Diffracted or transmitted radiation 44DT issues through at least one of the first and second windows, 43W1 and 43W2. Optionally, a portion of the sample 42 that has passed through the channel 47 is collected in a reservoir 49 located adjacent to the exit aperture 48EX. The sample flow stops, or is substantially reduced, when the actuator vibration stops.

FIG. 4 illustrates provision of two spaced apart, substantially parallel, transparent windows as part of a sample holder 41 that is open at two ends of the sample holder to permit a sample to flow along a sample holder channel 47. FIG. 4 also illustrates channel flow within a capillary, having substantially transparent walls and serving as a sample holder. The sample material within the capillary may be rotated about a channel axis and/or vibrated and/or translated at a selected frequency.

Figure 5:
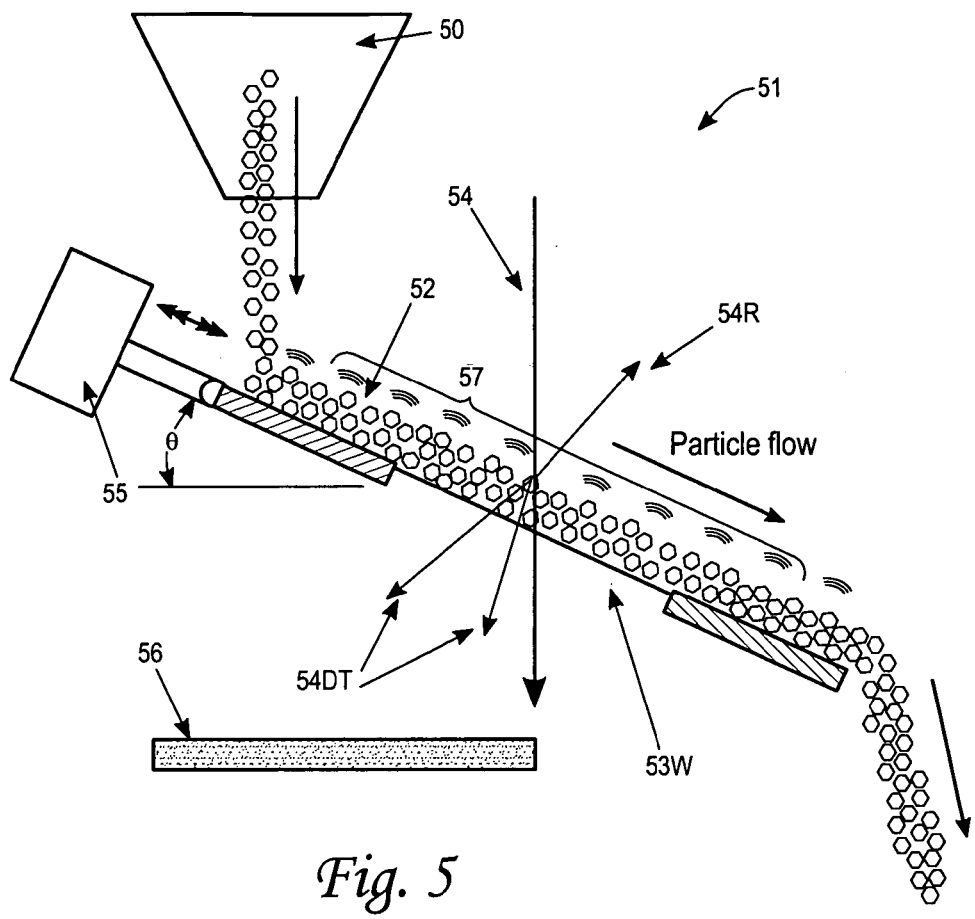

FIG. 5 is a sectional side view of a sample holder 51 that provides a channel 57, for flow from a reservoir 50 of a powder sample 52. The channel 57 is defined in part by a transparent window 53W that is oriented at a selected non-zero angle $\theta$ ($0<\theta<\pi T/2$) relative to a local horizontal plane. The sample 52 is preferably deposited in the channel 57 upstream from the window 53W. Flow of the sample 52 is provided by a selected combination of gravity and vibrations provided by an actuator 55, operated in a parallel or perpendicular excitation mode. Vibration and gravity result in an overall flow of material, in addition to random motion of the grain and convective internal flows. Electromagnetic radiation 54 in a selected wavelength region, incident on the sample 52 and the window 53W, is reflected as radiation 54R, received by a detector 56, and/or is diffracted and/or transmitted as radiation 54DT that is received by a another detector. The sample flow stops, or is substantially reduced, when the actuator vibration stops.

Figure 6:
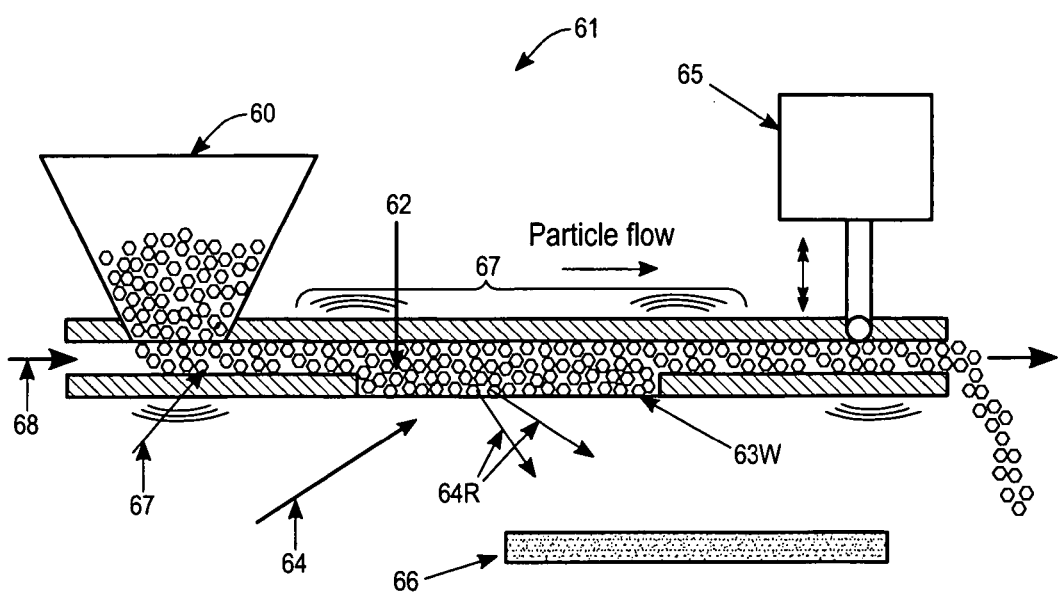
Figure 7:
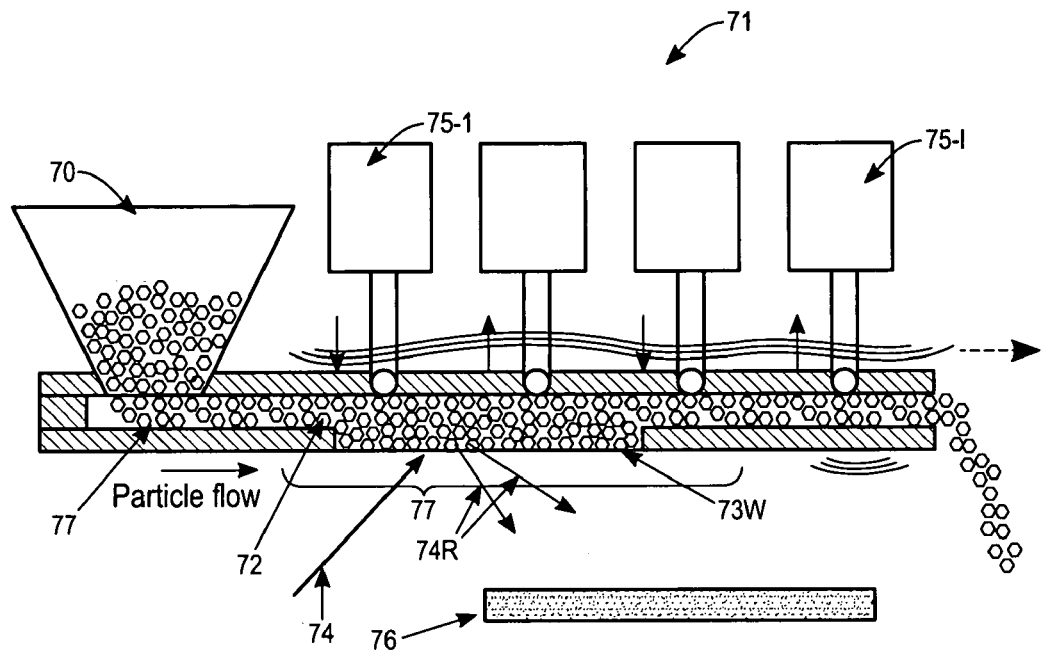

FIG. 6 is a sectional side view of a sample holder 61, similar to the sample holder 51 in FIG. 5, but with orientation angle 0 near 00, with sample flow aided by a flow 68 of a gas along an axis in a sample channel 67, optionally defined by one transparent window 63W. Flow of the sample 62 is provided by the gas flow and optionally by vibrations provided by an actuator 65, operated in a parallel or perpendicular excitation mode. The gas flow and vibrations result in an overall flow of material, in addition to random motion of the grain and convective internal flows. Electromagnetic radiation 64 in a selected wavelength region, incident on the sample 62 and the window 63W, is reflected as radiation 64R that is received by a detector 66. The sample flow stops, or is substantially reduced, when the actuator vibration stops.

FIG. 7 is a sectional side view of a sample holder 71, similar to the sample holder 61 in FIG. 6, but with two or more actuators 75-i(i=1, . . . I; I$\leq$2) that are operated in synchronism to generate one or more waves in the sample that move along a channel 77 in a selected direction (downstream and/or upstream). The sample flow stops or is substantially reduced when the synchronization of the actuators is such that the wave is no longer propagating. Direction of the flow can be controlled by changing the direction of wave propagation.

Figure 8:
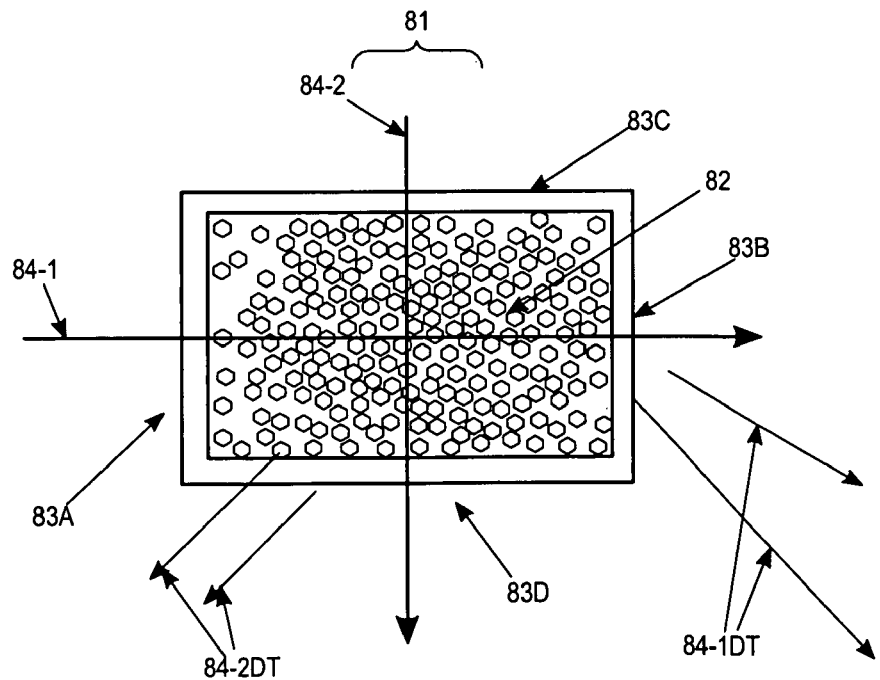

FIG. 8 is a top view of a sample holder 81 in which a channel (not shown) is defined by (1) first and second spaced apart, transparent windows, 83A and 83B, that face each other and (2) third and fourth spaced apart, transparent windows, 83C and 83D, that face each other, where a normal to the plane of the first window is transverse to a normal to the plane of the third window. First electromagnetic radiation 84-1 in a first selected wavelength region, incident on the sample 82 and on the first and second windows, 83A and 83B, is diffracted and/or transmitted as radiation 84-1 DT. Second electromagnetic radiation 84-2 in a second selected wavelength region, incident on the sample 82 and the third and fourth windows, 83C and 83D, is diffracted and/or transmitted as radiation 84-2DT. The first wavelength region and the second wavelength region may coincide, may partially overlap, or may be isolated from each other. Use of first and second electromagnetic radiation beams, 84-1 and 84-2, allows simultaneous interrogation of the sample 82 using two wavelength regions. One or more actuators (not shown in FIG. 8) may be provided to move the sample 82 along the channel. The spacing between the first and second windows, 83A and 83 B, and the spacing between the third and fourth windows, 83C and 83D, need not be the same.

The first and second windows in FIG. 8 may have different light transmission characteristics so that the second window acts as a filter for light incident on this window. For example, light diffracted from the sample may include K$\alpha$ and K$\beta$ radiation, separated in wavelength, and one of these two contributions to diffracted light may be suppressed by use of an appropriate light filter in the second window. In another example, the second window may act as a filter for sample fluorescence radiation that is incident of this window. The third and fourth windows may be similarly configured relative to each other.

Measurements of diffraction, fluorescence and infrared spectroscopy, as well as measurements of transmission/absorption and/or reflection (preferably using visible and/or infrared light), can be performed using the sample holder shown in any of FIGS. 1–8.

In any of FIGS. 1–8, the sample may be immersed in a liquid within the sample holder. The grains in the sample (and, optionally, the liquid) are again vibrated, or otherwise set in motion, and will tend to rotate within and move through the liquid. Images of the rotating individual grains can be analyzed to estimate a diameter of an individual grain and to provide information on the statistics of the distribution of grain diameters.

Figure 9A:
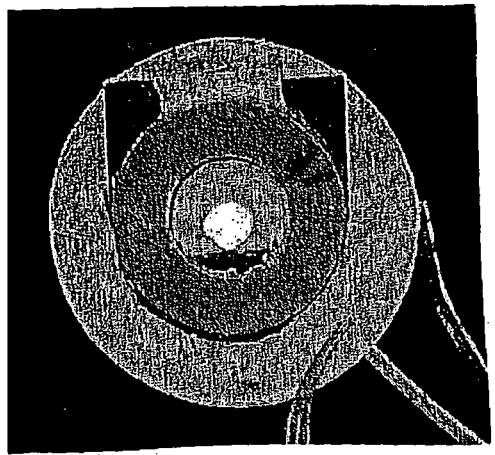
FIGS. 9A–9C are photographs showing a proof-of-concept apparatus.
Figure 9B:
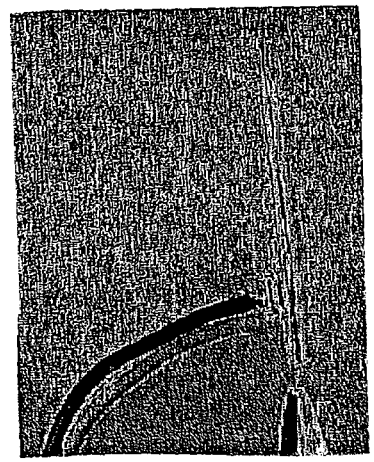
Figure 9C:
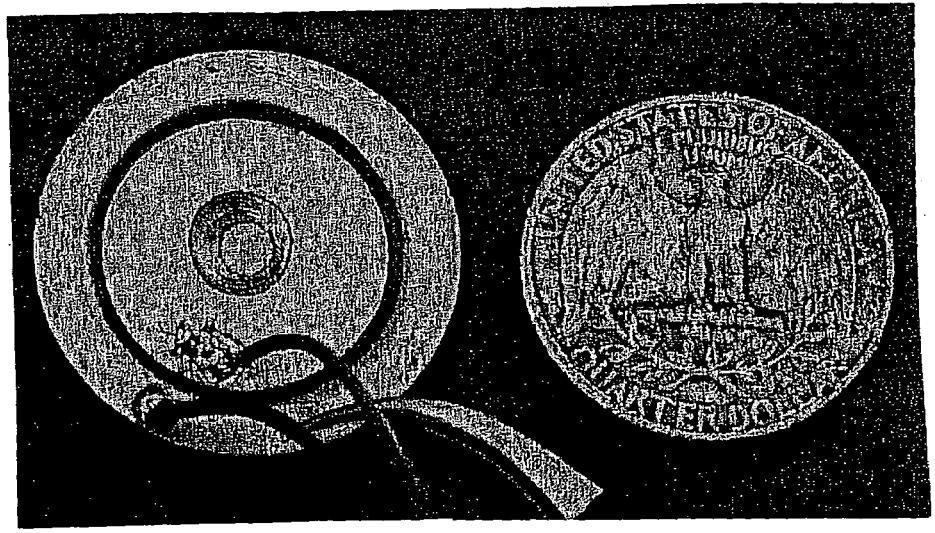

Alternatively, the sample may be immersed in a liquid having an arbitrary, but known, refractive index. A minimum refractive index value and a maximum refractive index value for the sample material can be estimated from the combined diffraction (within the sample grains) and refraction (at a grain-liquid interface). This approach is useful in estimating a range of refractive indices for a material that is only available as a powder or collection of grains. FIG. 9 illustrates a proof-of-concept convective motion system built from a modified piezoelectric buzzer actuator and vessel made with two thin Mylar windows spaced 0.2 mm apart. This sample holder was evaluated in a prototype CheMin instrument. Some results of use of this system are discussed in Example 1.

Figure 10:
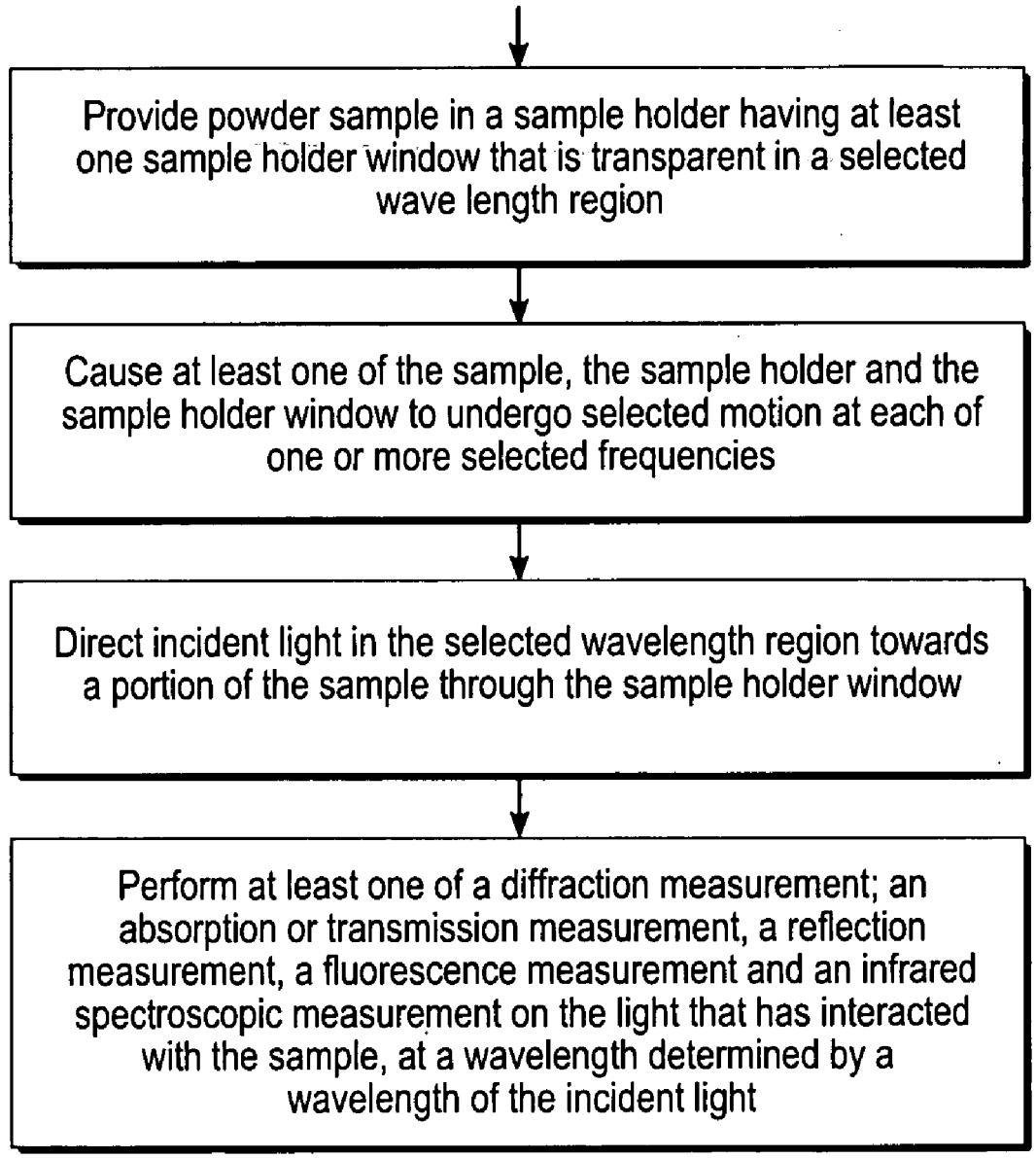
FIG. 10 is a flow chart of a procedure for practicing the invention.

FIG. 10 is a flow chart of a simplified procedure for practicing the invention. In step 101, a powder sample is provided in a sample holder that has at least one window that is substantially transparent to electromagnetic radiation in a selected wavelength region ("light"). In step 102, at least one of the sample, the sample holder and the sample holder window is caused to undergo selected motion (vibration, translation, rotation, etc.) at each of one or more selected frequencies, to cause sample grains to move in a random manner relative to each other. In step 103, incident light in the selected wavelength region is directed toward a portion of the sample in the sample window. In step 104, at least one of a diffraction measurement, a transmission or absorption measurement, a reflection measurement, a fluorescence measurement and an infrared spectroscopic measurement is performed on the incident light that has interacted with the sample, at a wavelength corresponding to, or determined by, a wavelength of the incident light. Optionally, the corresponding wavelength for measurement is chosen to be (1) a wavelength of the incident light or (2) a wavelength equal to an expected fluorescence wavelength for the sample or (3) a wavelength for an atomic or molecular energy level transition promoted by the incident light.

Granular materials show particular dynamic behavior when subjected to vibrations. One phenomenon observed is granular convection, wherein a translation motion, superimposed on a locally random motion, occurs in a granular medium contained in a vessel subjected to vibrations in a gravity field. The flow patterns observed in granular convection are similar to those observed in liquids being heated in a gravity field. This phenomenon is being extensively studied in non-linear physics, but few direct applications have been reported. Granular convection is used here to generate internal motion of the powder sample inside the sample holder during an XRD analysis, for example.

Practically speaking, a small volume of powder is contained in a small vessel that includes one or two spaced apart windows, transparent to a wavelength of an incident light beam and separated by tens to hundreds of micrometers. Appropriate vibrations in a gravity field generate convection patterns in the powder sample. This motion of the grains will present a large quantity of material to the interrogation beam over the time interval of the XRD, XRF or other analysis. In addition to an increase of the total amount of material being characterized, any given grain in the sample will be exposed to the incident light beam in many different crystalline orientations. FIGS. 3A and 3B are a front view and a sectional side view of a sample holder designed to generate convective motion in the sample. An actuator is connected to the sample holder, to the sample window and/or to the sample to generate vibrations or other random motion. The nature and the speed of movement of the powder sample depend on the geometry and elastic properties of the sample holder; how the sample holder is placed relative to the gravity field; and, the direction, magnitude, and frequency of the vibrational excitation.

Gravity-driven directional flow occurs as a consequence of the fluidization of a powder sample with vibrations. This results in a dramatic increase in flowability of the sample. This property is useful for material transport. Directional global flows are obtained when a driving force moves the material in an identifiable direction. In the simplest case, the driving force is gravity. An opening at the base of the vibrating holder allows powder to flow through. FIGS. 4 and 5 illustrate such systems, where the powder moves substantially parallel to a local gravity vector (FIG. 4) and moves in a direction that is substantially transverse to the local gravity vector (FIG. 5). The global flow velocity is primarily dependent on the size of the reservoir opening and the vibration intensity. The sample flow rate can easily be controlled with a valve or by changing the vibration intensity near the drain apertures.

Providing a controlled flow of a (dry) powder sample allows characterization of much larger quantities of the sample material than is allowed by regular sample handling techniques. This approach improves the fidelity of the analyzed sample. Depending on the design of the sample holder, the global flow of powder through the system can happen in conjunction with a convective flow and random grain motions.

When gravity is not present or is not appropriate, a slow, controlled flow of gas (preferably inert) through the sample holder can be used to move the material in a desired direction, as illustrated on FIG. 6. The flow of material can be controlled either by the vibration intensity and/or the gas flow velocity.

Propagation of vibration waves may also be used to implement powder transport, as shown on FIG. 7, where a sequence of two or more synchronized actuators vibrates a tube or thin vessel so that propagating waves are generated. The combination of vibrations and wave propagation will result in an overall flow of material. The material flow stops when the waves are not present or are no longer propagating. The direction of the flow can be reversed by changing the synchronization of the actuators to reverse the direction of wave propagation. Control of flow and/or reverse flow is useful in loading or unloading a sample holder with powder.

The nature and the speed of movement of the powder sample depends, in part, on the geometry and the elastic properties of the sample holder, how the sample is placed relative to the gravity field, and the direction, magnitude and frequency of the vibrational excitation.

Proof-of-concept prototypes of these systems were built using commercial piezoelectric devices, and the sample holder was designed to generate convective motion in the sample. An actuator was connected to the sample holder to generate vibrations. The nature and the speed of the movement of the powder depend on the geometry and elastic properties of the sample holder, how it is placed relative to the gravity field and the direction, magnitude, and frequency of the vibrational excitation. FIG. 9 shows one of these devices, built from a modified buzzer actuator on which mylar windows were mounted. A buzzer driver was modified to control the intensity of vibration (excitation at 300 Hz in one example). Despite limited control over the direction and frequency of vibrational excitation, convective motion of the powder is easily generated and observed in a microscope.

EXAMPLE 1

Example 1 shows two-dimensional diffraction patterns collected with an NASA CheMin system. The instrument was fitted with a vibrating sample holder loaded with a crushed and sieved quartz sample having a grain size range of 61–124 μm. This sample is very coarse-grained relative to what is considered acceptable for XRD. The analytical volume in the instrumental configuration used here is a cylinder approximately 70 μm in diameter and 200 μm thick. Thus, only a few grains of powder are exposed to the X-rays at any time.

With the actuator turned off, the absence of a clear diffraction pattern is consistent with what would be obtained from a coarse-grained sample such as this. By comparison, an ideal two-dimensional powder diffraction pattern would show continuous rings centered on the beam axis (center-top of the image). With the actuator turned on, the patterns do indeed show the continuous rings.

Figure 11B:
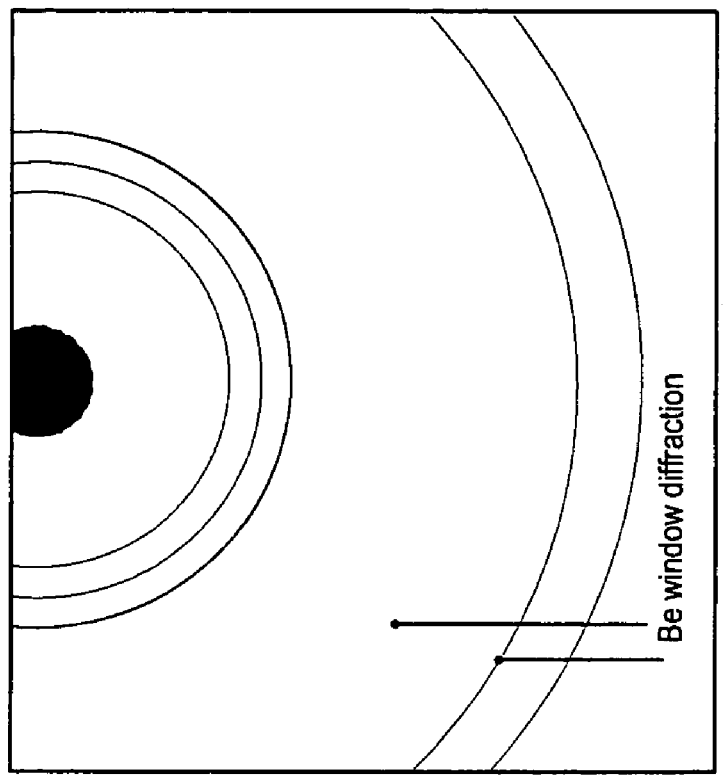
FIGS. 11A and 11B illustrate a diffraction pattern produced without and with vibration according to the invention.
Figure 11A:
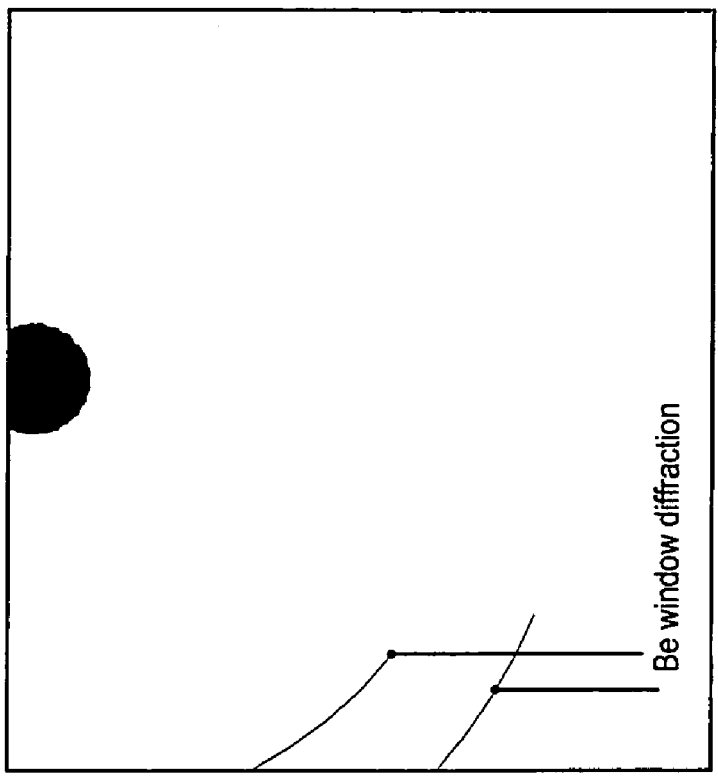

A diffraction pattern was recorded with a miniature XRD/XRF instrument (CheMin breadboard); 10 min exposure, 20W tube, 70 μm diameter spot, 70 μm aperture. The sample is crushed quartz, sized between 61 and 124 μm; without vibration FIG. 11A), and with vibration at 300 Hz, pulsed at 1 Hz with 50 percent duty cycle (FIG. 11B).

Figure 12:
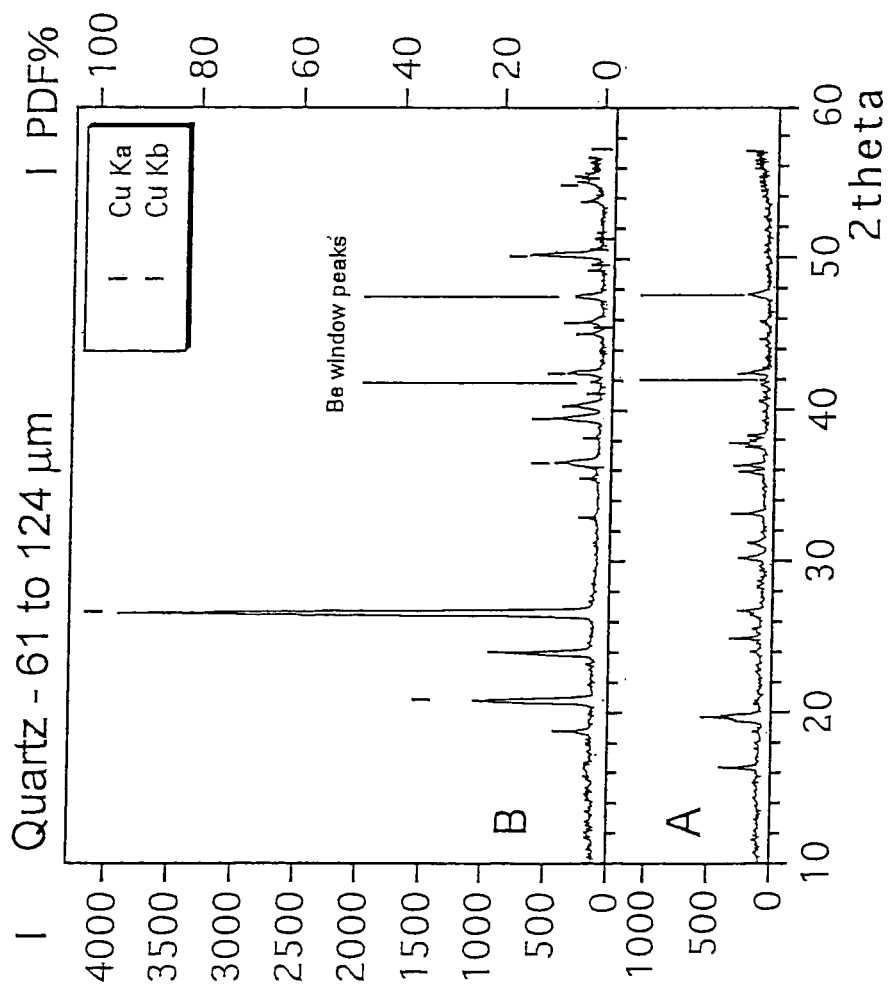
FIG. 12 graphically illustrates a diffraction pattern produce by the system, without vibration (A) and with vibration (B) according to the invention.

These two-dimensional diffraction patterns were integrated into conventional 2θ scans, shown graphically in FIG. 12, parts A and B. The data collected in a vibrating mode (labeled B) show all the quartz diffraction peaks of Cu(Kα) and Cu(Kβ), with the appropriate relative intensities. These data would be adequate for phase identification or even a detailed study of the crystalline structure of the mineral.

This spectacular improvement of the diffraction data offered by the vibrating sample holder will be further increased with better control of the vibration and improved vessel design. It is also expected that the difference between unshaken and shaken samples will be higher with longer acquisition times. Indeed, the presented data were collected in 10 min., an unusually short time for XRD analysis.

The results show that using a vibrating sample holder will lead to much improved XRD data, shorter integration times, simpler sample handling procedure, and much simpler requirements for the sample preparation. Material received from a drill or a crusher could be sieved to a reasonable grain size (for instance <200 μm) and analyzed without further preparation.

Control of the Sample Thickness

The proposed technology provides unique means of adjusting the "optical thickness" of the sample during the analysis. The sample thickness is a very important parameter for transmission XRD. If the sample is too thick, the radiation is absorbed in the material and the XRD signal is reduced. On the other hand, if the sample is very thin, less material is placed in the X-ray beam. For the particular case of a flat sample with perpendicular incident X-ray beam such as used in the CheMin or other miniaturized XRD/XRF instruments, it can be shown that the optimum is obtained when $x=1/\mu$, with μ linear absorption coefficient factor which depends on the sample chemical composition and density and the type of radiation used.

For a given X-ray wavelength, this optimum varies significantly depending on the sample chemical composition and density. With conventional XRD sample handling techniques, the thickness of the sample is predetermined during sample preparation. This innovation provides a unique means of adjusting the "optical thickness" of the sample during the analysis. The control of sample thickness can be made by either one or both of the following:

Control of the density of the material in the analytical volume; this is done by adjusting the intensity of vibration of the powder (high intensity vibration=dispersion; low intensity vibration=compaction). This method affects the apparent μ of the granular material).

Control of the thickness of the analytical volume by physically changing the gap between windows; this mechanical control can be done with additional actuators, or with the actuator used to generate the vibration.

The feedback signal for the regulation of the optical thickness is either obtained from the integrated diffracted intensity measured from the detector, or the transmission ratio of the direct beam measured by a specific detector. With the flat sample configuration, the optimum thickness condition ($x=1$ μm) results in a transmitted intensity of the direct beam of $1/e \approx 0.37$. A direct beam intensity $I_0$ can be measured prior to insertion of the sample. After sample insertion the optical thickness is adjusted to obtain a transmission ratio of $I/I_0=0.37$. The direct beam intensity detector can be embedded in the beam stop assembly.

Another consequence of the vibration-induced fluidization of powder is a dramatic increase in its flowability. This property can be used to load and unload samples in the instrument. The sample are loaded outside the instrument in a funnel shaped loading container. A sieve is incorporated in the funnel to reject particles above a selected diameter. The base of the funnel can be connected to the sample holder of the XRD/XRF, or other analytical instrument. Vibration of the funnel/sample holder assembly causes the powder to flow to the analysis region.

After analysis, an evacuation aperture at the base of the vibrating holder is opened to allow the powder to be drained out of the instrument. The sample holder prototype shown in FIG. 2 was loaded and unloaded in this fashion. Very little powder remains in the vessel after the sample is removed in this way. If cleaning of the sample holder is required to remove traces of powder, optional flushing with a dry gas can be provided.

Alternatively, the powder can be transported into the sample holder and/or transported out of the sample holder using convective flow that is implemented by gas flow or by one, two or more actuators operated in synchronism. This approach is especially attractive for automated loading and/or unloading of a sample holder with powder.

What is claimed is:

1. A method for analyzing a powder sample of a substance, the method comprising:
   providing a powder sample of a substance in a sample holder that has at least one window that is substantially transparent to electromagnetic radiation in a selected wavelength region;
   performing at least one of vibration motion, rotation motion and translation motion ("motion") on at least one of the sample, the sample holder and the at least one sample holder window at each of one or more selected motion frequencies, to thereby cause grains of the sample to move in a random manner relative to each other;
   directing electromagnetic radiation having a wavelength in the selected wavelength region ("incident light") toward a portion of the sample shown in the at least one window; and
   for at least one selected motion frequency, performing at least one of a diffraction measurement, a transmission or absorption measurement, a reflection measurement, a fluorescence measurement and a spectroscopic measurement on incident light that has interacted with the sample, at a wavelength determined by a wavelength of the incident light.

2. The method of claim 1, further comprising choosing said wavelength determined by said incident light wavelength to be substantially equal to said incident light wavelength.

3. The method of claim 1, further comprising choosing said wavelength determined by said incident light wavelength to be an expected wavelength for fluorescence of said sample when exposed to irradiation by said incident light.

4. The method of claim 1, further comprising choosing said wavelength determined by said incident light wavelength to be an expected Raman shift wavelength for Raman spectroscopy performed on said sample using irradiation by said incident light.

5. The method of claim 1, further comprising performing said at least one motion on said sample holder in a direction that is substantially parallel to an axis of said sample holder.

6. The method of claim 1, further comprising performing said at least one motion on said sample holder in a direction that is substantially perpendicular to an axis of said sample holder.

7. The method of claim 1, further comprising rotating said sample holder at a selected angular frequency while said at least one of said sample, said sample holder and said sample holder window is undergoing said motion.

8. The method of claim 1, further comprising translating said sample at a selected translation rate while said at least one of said sample, said sample holder and said sample holder window is undergoing said motion.

9. The method of claim 1, further comprising:
providing said sample holder with a second window on a surface of said holder that faces and is opposed to said first window, is spaced apart from said first window by a selected distance, and is substantially transparent to radiation in a second selected wavelength region;
performing said measurement, using transmission or absorption of said incident light through said first window, at a selected incidence angle relative to a normal to a plane of said first window, through said sample and through the second window.

10. The method of claim 9, further comprising selecting said second wavelength region to be substantially equal to said first wavelength region.

11. The method of claim 9, further comprising selecting said second wavelength region to include an expected wavelength for fluorescence of said sample when exposed to irradiation by said incident light.

12. The method of claim 9, further comprising selecting said second wavelength region to include an expected Raman shift wavelength for light emitted by said sample when exposed to irradiation by said incident light.

13. The method of claim 9, further comprising
providing said sample holder with a third window and with a fourth window that faces and is opposed to the third window, is spaced apart from the third window by a selected second distance, and is substantially transparent to radiation in a third selected wavelength region; and
performing at least one of a transmission or absorption measurement of said incident light and a fluorescence measurement of said incident light that passes through the third window, through said sample and through the fourth window.

14. The method of claim 13, further comprising selecting said second distance to be different from said first distance, to thereby provide at least two different sample thicknesses to interact with said incident light.

15. The method of claim 9, further comprising
providing said sample holder with a third window and with a fourth window that faces and is opposed to the third window, is spaced apart from the third window by a selected second distance, and is substantially transparent to radiation in a third selected wavelength region; and
performing at least one of a transmission or absorption measurement of said incident light and a fluorescence measurement of said incident light that passes through the third window, through said sample and through the fourth window, substantially simultaneously with performance of said measurement for said light incident on said first window.

16. The method of claim 1, further comprising providing said sample holder as comprising a capillary tube that receives said sample and allows said motion of said sample within the capillary tube.

17. The method of claim 1, further comprising performing said measurement by a process comprising:
passing said incident light through said at least one window from a first window side to a second window side at a selected incidence angle relative to a normal to a plane of said at least one window;
allowing said incident light to be diffracted by at least one grain of said sample; and
passing said, incident light through said at least one window from the second window side to the first window side.

18. The method of claim 1, further comprising performing said measurement, using reflection of said incident light.

19. The method of claim 1, further comprising providing a selected flow of a gas in a selected direction within said sample holder to thereby promote transport of a portion of said sample in the selected direction.

20. The method of claim 1, further comprising:
orienting an axis of said sample holder in a direction having a non-zero vector component that is parallel to a vector of local gravitational force; and
performing said motion, on said sample holder so that said powder sample is caused to move from a first location to a second location that is substantially below the first location under a combined influence of said motion and the gravitational force.

21. The method of claim 1, further comprising:
providing an array of at least first and second spaced apart vibration actuators along an axis of said holder, where each actuator vibrates at the same one of said selected frequencies and has an independently selectable phase; and
selecting the phase of the first actuator relative to the phase of the second actuator to promote propagation of a wave along the holder axis.

22. The method of claim 1, further comprising providing said at least one window with a thickness that lies in a range 1–20 μm.

23. The method of claim 1, further comprising:
suspending said powder sample in a selected liquid, having a selected liquid refractive index, within said sample holder;
performing said measurement on at least one grain in said powder sample with a first angular orientation and with a second angular orientation of the grain relative to said at least one window; and
estimating a maximum refractive index and a minimum refractive index for the at least one grain from the measurements with the first and second angular orientations.

24. The method of claim 1, further comprising orienting an axis of said sample holder so that at least a second portion of said sample that is initially outside said sample holder is caused to move into said sample holder.

25. The method of claim 1, further comprising orienting an axis of said sample holder so that at least a second portion of said sample that is initially in said sample holder is caused to move out of said sample holder.

* * * * *